United States Patent
Hladio et al.

(10) Patent No.: US 12,053,273 B2
(45) Date of Patent: Aug. 6, 2024

(54) SYSTEM AND METHOD TO REGISTER ANATOMY WITHOUT A PROBE

(71) Applicant: INTELLIJOINT SURGICAL INC., Kitchener (CA)

(72) Inventors: Andre Novomir Hladio, Waterloo (CA); Ki Don Son, Waterloo (CA); Richard Tyler Fanson, Stoneycreek (CA); Andrew Welsh, Kitchener (CA)

(73) Assignee: Intellijoint Surgical Inc., Kitchener (CA)

( * ) Notice: Subject to any disclaimer, the term of this patent is extended or adjusted under 35 U.S.C. 154(b) by 872 days.

(21) Appl. No.: 16/562,794

(22) Filed: Sep. 6, 2019

(65) Prior Publication Data

US 2020/0077924 A1 Mar. 12, 2020

Related U.S. Application Data

(60) Provisional application No. 62/728,179, filed on Sep. 7, 2018.

(51) Int. Cl.
*A61B 5/11* (2006.01)
*A61B 5/00* (2006.01)
*A61B 90/00* (2016.01)
*G06T 7/33* (2017.01)

(52) U.S. Cl.
CPC .......... *A61B 5/1114* (2013.01); *A61B 5/0077* (2013.01); *A61B 5/1121* (2013.01); *A61B 90/37* (2016.02); *A61B 90/39* (2016.02); *G06T 7/337* (2017.01); *A61B 2090/3937* (2016.02); *A61B 2090/3983* (2016.02); *G06T 2207/30008* (2013.01); *G06T 2207/30204* (2013.01)

(58) Field of Classification Search
CPC ... A61B 5/1114; A61B 5/0077; A61B 5/1121; A61B 90/37; A61B 90/39; A61B 2090/3937; A61B 2090/3983; A61B 34/25; A61B 46/10; A61B 2034/2057; A61B 2034/252; A61B 2090/365; A61B 2090/372; A61B 2090/502; G06T 7/337; G06T 2207/30008; G06T 2207/30204; G06T 2200/24; G06T 2207/10016; G06T 7/73; G06T 2207/20101
See application file for complete search history.

(56) References Cited

U.S. PATENT DOCUMENTS

| | | | | |
|---|---|---|---|---|
| 2007/0249967 A1* | 10/2007 | Buly | ............... | A61B 5/1121 600/595 |
| 2014/0002390 A1* | 1/2014 | Lee | ............... | G06F 3/041 345/173 |
| 2018/0000613 A1* | 1/2018 | Lunau | ............... | A61B 5/103 |
| 2018/0185100 A1* | 7/2018 | Weinstein | ............... | A61F 2/461 |
| 2019/0000372 A1* | 1/2019 | Gullotti | ............... | A61B 17/7091 |

* cited by examiner

*Primary Examiner* — Baisakhi Roy
*Assistant Examiner* — Kaitlyn E Sebastian (57) ABSTRACT

Systems and methods provide registration of anatomical points of interest to a surgical navigation system using a camera only without a separate tracked probe. Graphical elements are overlaid on real time images of patient anatomy. Workflow directs the capture of image registration data (pose data) when the graphical elements are aligned. The graphical elements may represent positional features of the camera such as one or more axis positions.

9 Claims, 8 Drawing Sheets

SYSTEM AND METHOD TO REGISTER ANATOMY WITHOUT A PROBE

CROSS-REFERENCE

This application claims the benefit of U.S. Provisional Application No. 62/728,179 filed Sep. 7, 2018 entitled "System and Method to Register Anatomy without a Probe", the content of which is incorporated herein in its entirety.

FIELD

The present application relates to systems and methods for localizing objects in three dimensional (3D) space and more particularly to a system and method to register anatomy without a probe.

BACKGROUND

Surgical navigation and related systems (generally surgical navigation systems herein) assist surgeons and other users to improve patient outcomes. Objects such as tools and parts of a patient's anatomy are trackable in a 3D space (e.g. a coordinate system) defined by the surgical navigation system from images received from a camera. The pose of an object in up to 6 degrees of freedom (DOF) may be registered in the 3D space. Typically a probe having a tracker coupled thereto is used to point to anatomical reference points on the anatomy to register the anatomy in the 3D space. The anatomy usually has a tracker associated in a fixed relationship to the anatomy. In one example the tracker may be fixed to the anatomy.

Probes must be sterile for use in the surgical environment. They must be robustly constructed. The surgical navigation system includes definitional data therefor to enable a determination of the pose of the tip of the probe from the pose of the probe's tracker. Should this relationship between probe tracker and probe tip be disturbed, measurements may be inaccurate or require a (new) calibration.

SUMMARY

Systems and methods provide registration of anatomical or other points of interest to a surgical navigation system using a camera only without a separate tracked probe. Graphical elements are overlaid on real time images of patient anatomy. Workflow directs the capture of image registration data (pose data) when the graphical elements are aligned with the anatomy. The graphical elements may represent positional features of the camera such as one or more axis positions.

The intellijoint design trademark shown in the drawings and the trademark INTELLIJOINT are trademarks of Intellijoint Surgical Inc. and all rights are reserved.

DESCRIPTION

Figure 1:
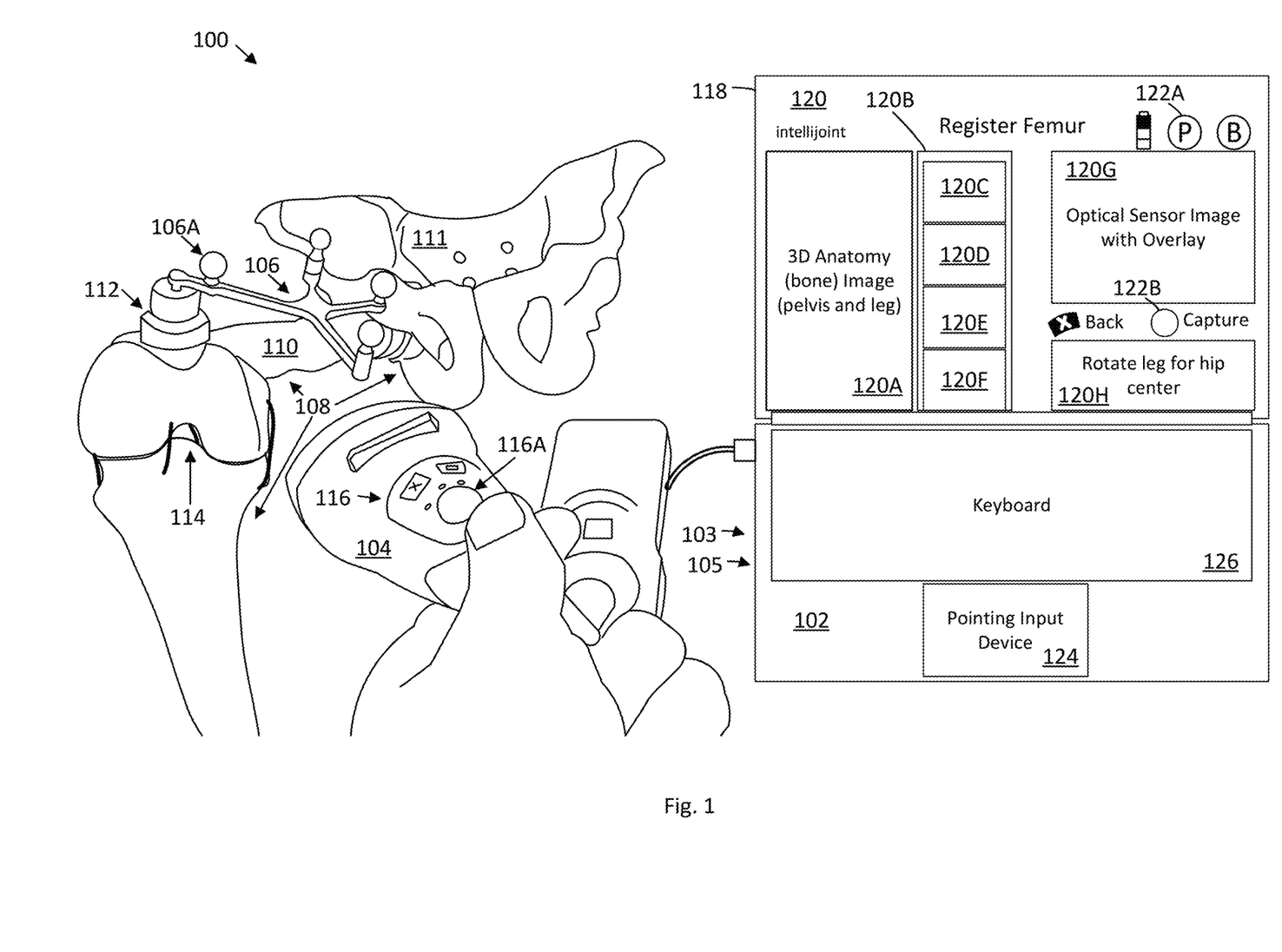
FIG. 1 is an illustration of a surgical navigation system in accordance with the present teachings.

FIG. 1 is an illustration of a surgical navigation system 100 in accordance with the present teachings. The surgical navigation system 100 comprises a computing device 102 such as a laptop having a processor 103. The processor 103 is an example of a processing device and may comprise one or more microprocessors, CPUs, GPUs, or other programmable devices or hardwired processing devices. The computing device 102 and hence the processor 103 are coupled to a camera 104. The computing device 102 may take other forms than a laptop such as a tablet, workstation, etc. The computing device 102 comprises a storage device 105 (e.g. memory) storing instructions. When executed by the processor 103 the instructions configure operations of the computing device 102 (i.e. the surgical navigation system 100) as described further herein. Though configured via software, the surgical navigation system 100 could employ a more hardware centric model.

A tracker 106 is coupled to an anatomy 108 of a patient (represented in FIG. 1 by a physical or demonstration model used to test and/or demonstrate system 100). The tracker 106 is mounted to the anatomy, namely a femur 110 at and end (e.g. knee end) distal from a hip 111. It may be releasably mounted such as via a quick connect mechanism 112. In the present surgical navigation system 100 the tracker 106 is comprised of spaced reflective spheres (e.g. 106A) for detection in images communicated to the processor 103 from the camera 104. The camera 104 is a monocular camera and the camera 104 may work in the IR spectrum or other spectra.

The tracker 106 is mounted adjacent the knee 114 so that the tracker 106 is visible in a field of view of the camera 104 when directed at the knee 114. It is understood that if a tight shot of the knee 114 is desired, (e.g. where the camera 104 is proximate to the knee 114), the tracker's spheres (e.g. 106A) may not be within the field of view. In the present example the camera 104 comprises a fixed focal length lens where zoom in an out is performed by adjusting the distance of the camera 104 to the object. Though not shown, in a surgical setting the camera 104 (and at least part of the cabling (not shown)) may be shrouded for sterility. For example, the camera 104 may be enclosed in a sterile drape having an optically transparent window in alignment with the optical window or lens of the camera.

The camera 104 is provided with user interfaces 116 such as a button 116A to invoke a processor operation. The user interfaces 116 may function through a sterile drape. The computing device 102 comprises a display device 118 (which may be a gesture receiving device (e.g. touch screen) for input). Display device 118 may present a graphical user interface 120 comprising one or more regions and/or sub-regions (e.g. 120A, 120B, 120C, 120D, 120E, 120F, 120G, 120H, etc.). Icons (e.g. 122A, 122B, etc.) and other GUI elements may be provided within the GUI 120 (e.g. within such regions and/or sub-regions) as controls to receive user input, such as via a point device (e.g. 124) and/or to display information to a user, such as instructions in region 120H. Input may also be provided via a keyboard 126.

Input from camera 104, pointing input device 124 or the keyboard 126 may invoke an operation of computing device 102. The operation may be a capture (e.g. identification and/or storage) of data by the processor 103 in response to workflow presented via the graphical user interface 120 on the display device 118 coupled to the processor 103. As shown on the display device 118, the GUI may integrate real time display of images (e.g. in region 120G) received from the camera 104 together with graphical and/or text elements such as workflow instructions and/or controls.

Further, the real time images may be augmented such as by overlaying graphical elements thereon (see FIGS. 2-8). In some examples the graphical elements may represent anatomical features registered to the surgical navigation system 100 or computed anatomical features from other registered or computed anatomical features. In some examples the graphical elements may represent camera features such as positional features including but not limited to an axis or axes thereof, a position of a light ray entering the camera, etc. The position of the light ray may coincide with the X-axis or central axis (or optical axis) of the line of sight of the camera (the central axis and X axis being coincident). In some examples the graphical elements may represent an object or features thereof in the field of view (e.g. highlighting the spheres of the tracker 106). Other features, measurements, instructions, labels, etc. may also be indicated by graphical elements overlaid on the real time images received from the camera 104. The images displayed may be processed (i.e. not raw images, per se) for example for contrast, brightness, unwarping, etc.

A suitable display device 118 may be a screen of the laptop (as shown) and/or a coupled monitor, a projector for projecting an image, a Virtual Reality (VR) display, heads-up display, etc.

Figure 2:
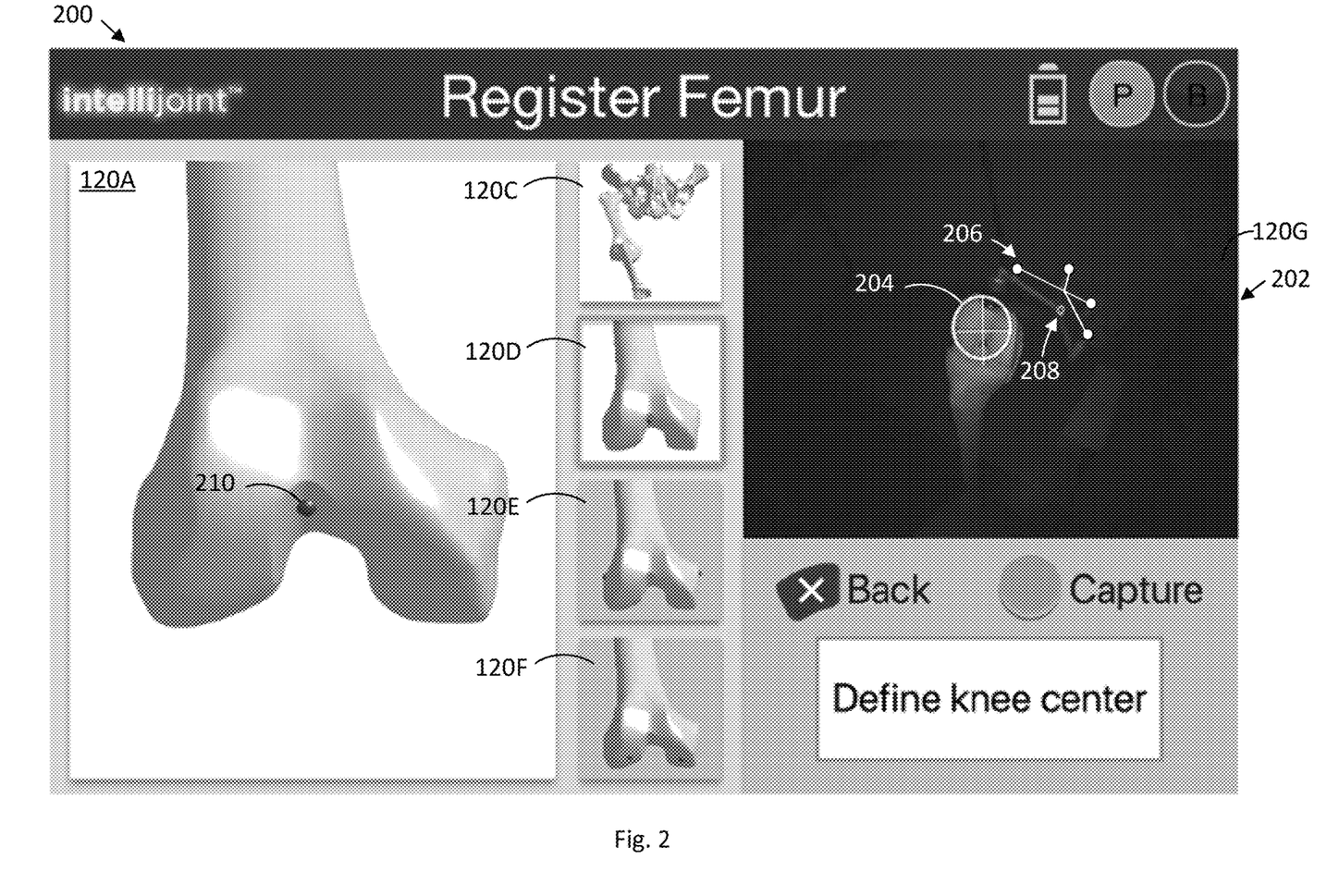
FIGS. 2, 3 and 4 are screenshots of workflow for operations to establish an anatomical reference point in a 3D space for images (e.g. register the anatomical reference point) as defined by the surgical navigation system.
Figure 3:
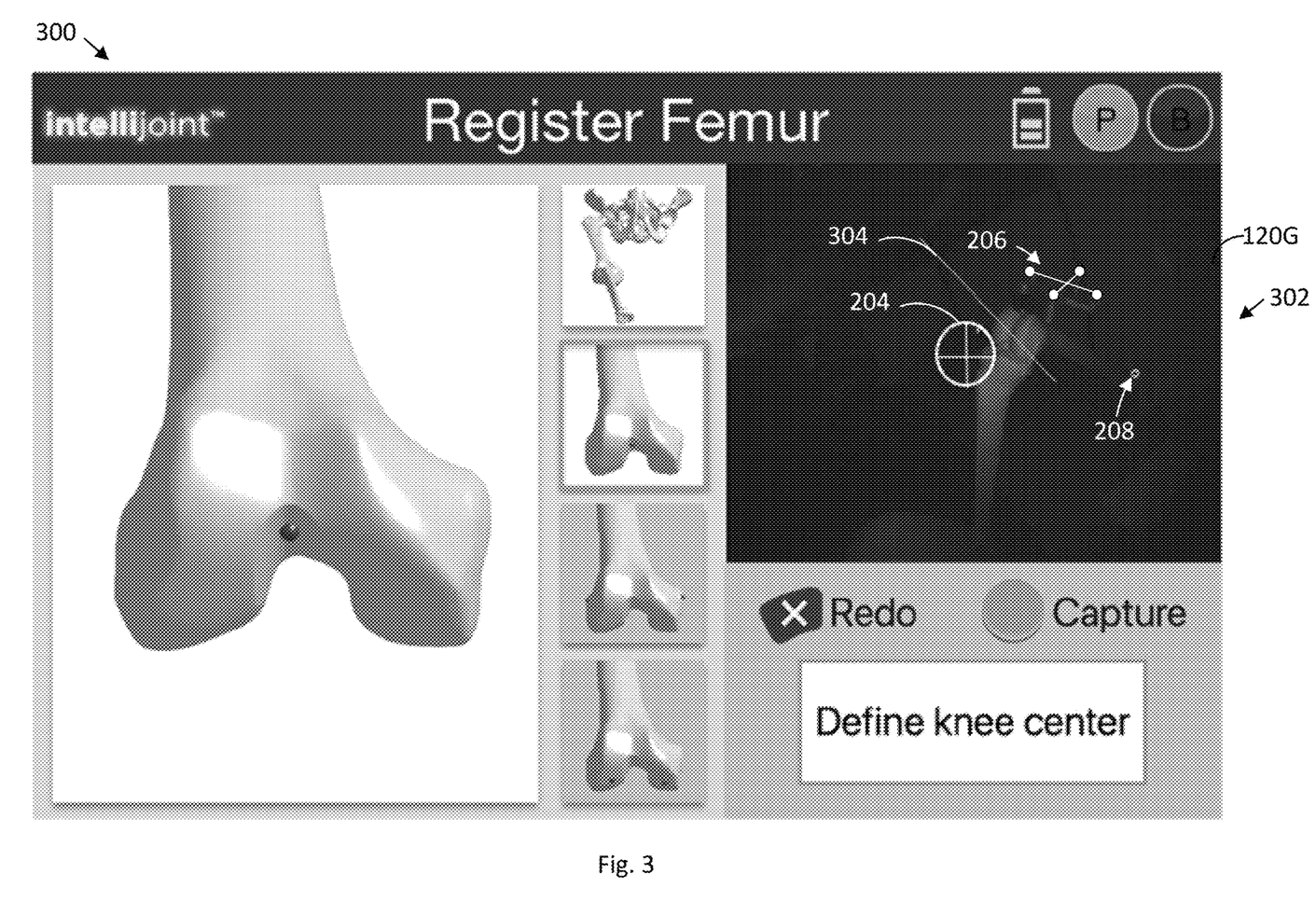
Figure 4:
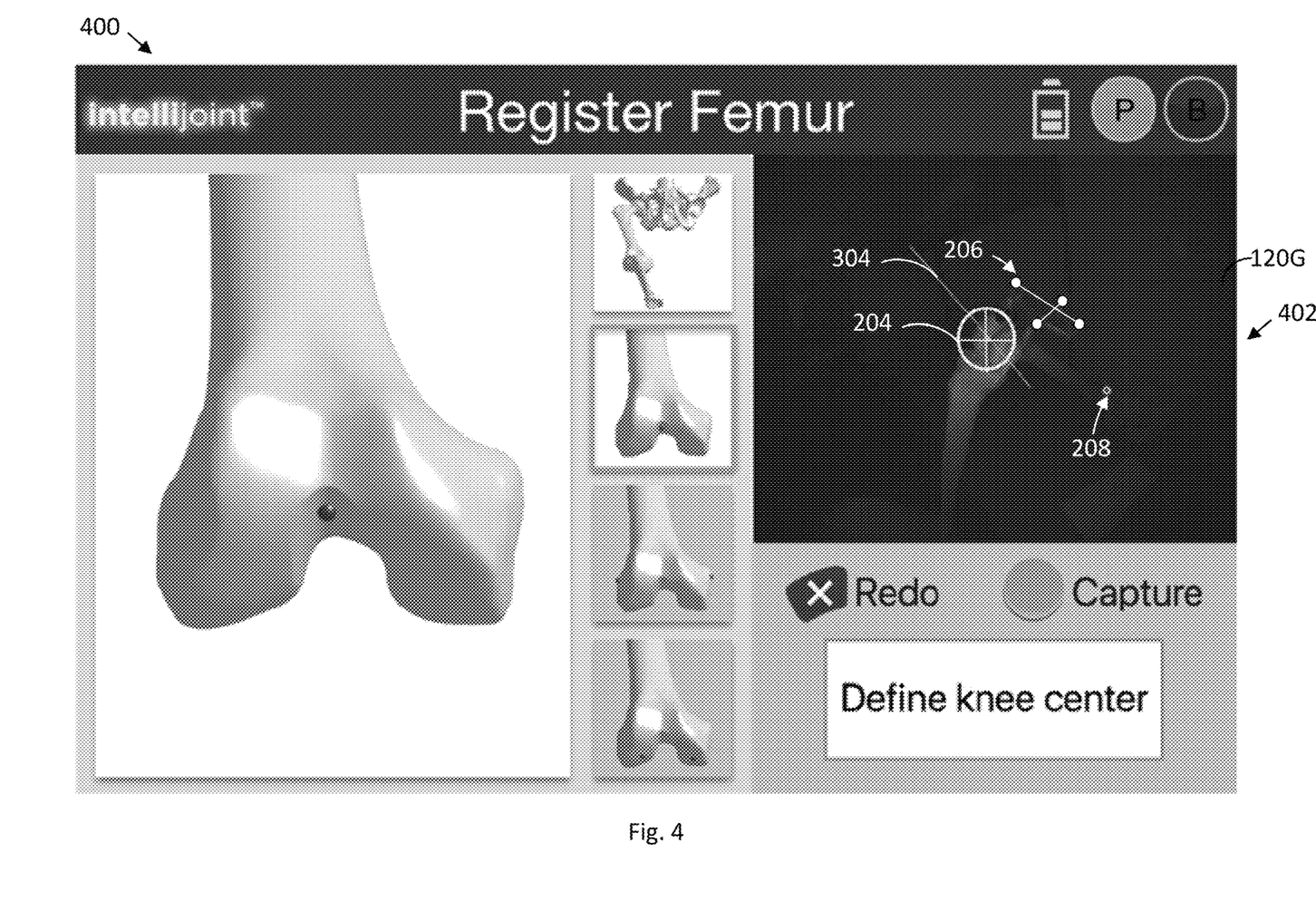

FIGS. 2-4 are screenshots 200, 300 and 400 of workflow for operations to establish an anatomical reference point in a 3D space for images (e.g. register the anatomical reference point) as defined by the surgical navigation system 100. While an anatomical reference point is described any point of interest may be registered.

FIG. 2 shows screenshot 200 to register an anatomical reference point which, in this example, is a knee center of the femur 110. In this screenshot 200 the camera image 202 in region 120G is overlaid with graphical elements (e.g. markers or indicators 204, 206, 208). Some graphical elements (e.g. connected circles 206) indicate the spheres of the tracker 106. In the present example, the camera 104 is an infrared (IR) camera and the relatively low visible light in the image can make some objects more difficult to see. Highlighting the spheres (e.g. 106A) of the tracker 106 may assist to instruct a user to keep the tracker 106 within the field of view of the camera 104.

Another marker or indicator 208 shows a hip center of rotation ("HCOR") as represented by an "O" or open circle shape. The HCOR may be registered using workflow (not shown) such as by rotating the femur 110 about multiple positions in the hip 111 while the camera 104 captures multiple instances of the position of the tracker 106 attached at the distal (knee) end. The processor 103 then computes the hip center of rotation as an intersection of respective vectors from the respective positions of the tracker 106. Multiple instances (of the tracker position) are captured and used to enhance accuracy.

In addition, a crosshair marker 204, an example of an alignment or targeting marker or indicator, is displayed to show a position of a light ray entering the camera 104 along its X axis. The crosshair marker 204 comprises a common sighting or targeting motif used to align one object such as a center axis of a camera's line of sight with a target 106 such as an anatomical reference point. The targeting marker 204 is aligned with (i.e. is directed to a position that is over) the anatomical reference point in FIG. 2.

In the present example, workflow for the registration is assisted by illustrations in region 120A. Such illustrations may be in the form of 3D anatomy images (e.g. model images). As seen in FIG. 2, sub-regions 102C to 102F show various 3D anatomy images (similar to large icons) associated with steps of the registration workflow. The GUI 118 may be configured to indicate progress through the workflow. In the present example, region 120D is shown as the selected or current step, having a box around the image in the region 120D and with the image shown on a white background. The anatomical image is also shown in enlarged form in region 120A. In this way the anatomical reference point of interest 210 (the knee center) for the step is shown in more detail. In region 120C, the respective anatomical image is shown on a white background but not highlighted. This sub-region is associated with the screen illustration of FIG. 1 and represents a completed step. Sub-regions 120E and 120F are shown with the respective images on a grey or darker background as these steps have yet to be performed. The GUI may be configured to invoke the workflow for that step by selecting the sub-region. Some sub-regions may not invoke the step or permit its performance until a prior step of the workflow is completed.

The surgical navigation system 100 establishes a working 3D space (a mathematical coordinate system) for images received from the camera 104. The processor 103 is provided with calibrations (e.g. definitional data) for use to determine the position of a light ray (e.g. the X Axis) entering the camera. The light ray is representable as a 3D vector in the 3D space relative to a tracker located in the image generated by the camera 104. The processor 103 receives images of the anatomy 108 of the patient including the tracker 106 where the tracker 106 is in a fixed position relative to the anatomy 108.

The position of an anatomical reference point (e.g. 210) or other point of interest may be established (registered) in the 3D space without using a probe (a surgical tool and a physical object) to point out the reference point.

According to a first example, by aligning the anatomical point of interest with the targeting marker 204 on the images (e.g. 202) from the camera 104, a 3D vector that the point of interest lies on can be determined (e.g. in response to input such as a button push from the camera 104). The input invokes the processor 103 to capture image registration data (e.g. images of the anatomy with the tracker 106 from which the position may be determined). Two such 3D vectors can be defined by capturing the positions of the light ray (i.e. the X axis) using two different camera positions where the two 3D vectors are different (not coincident). These 3D vectors or skew lines are then used to determine the position of the point of interest, ideally, where the two skew lines cross.

The processor 103 calculates an accurate estimate of the position by mathematically determining the average of the points on the respective skew lines that have the shortest distance to each other (e.g. by calculating the midpoint of a 3D vector representing the minimum Euclidean distance between the skew lines).

FIG. 3 shows the screenshot 300 including an image 302 from the camera 104 when defining the second 3D vector. The first light ray defined by the first 3D vector is represented by a graphical element (e.g. a first light ray indicator in the form of a line 304) overlaid on the images (e.g. 302) in real time.

With reference to FIG. 4 and screenshot 400, the targeting marker 204 is aligned with the position of the point of interest (the knee center) in the images (e.g. image 402), where the point also lies along line 304 representing the first 3D vector, and a second 3D vector is defined (e.g. in response to input such as a button push from the camera).

Thus, the operations perform to: display a marker 204, in real time, overlaid on a display of the images (e.g. images 302, 402 in GUI 120) from the camera 106, the marker 204 indicating the position of the light ray in the images 302, 402; define a first 3D vector for the light ray in response to input received indicating that the light ray is aligned with an anatomical reference point relative to the anatomy 108; define a second 3D vector of the light ray in response to input received indicating that the light ray is aligned with the anatomical reference point and where the second 3D vector is different from the first 3D vector; and calculate a position in the 3D space of the anatomical reference point using the first 3D vector and the second 3D vector.

Figure 5:
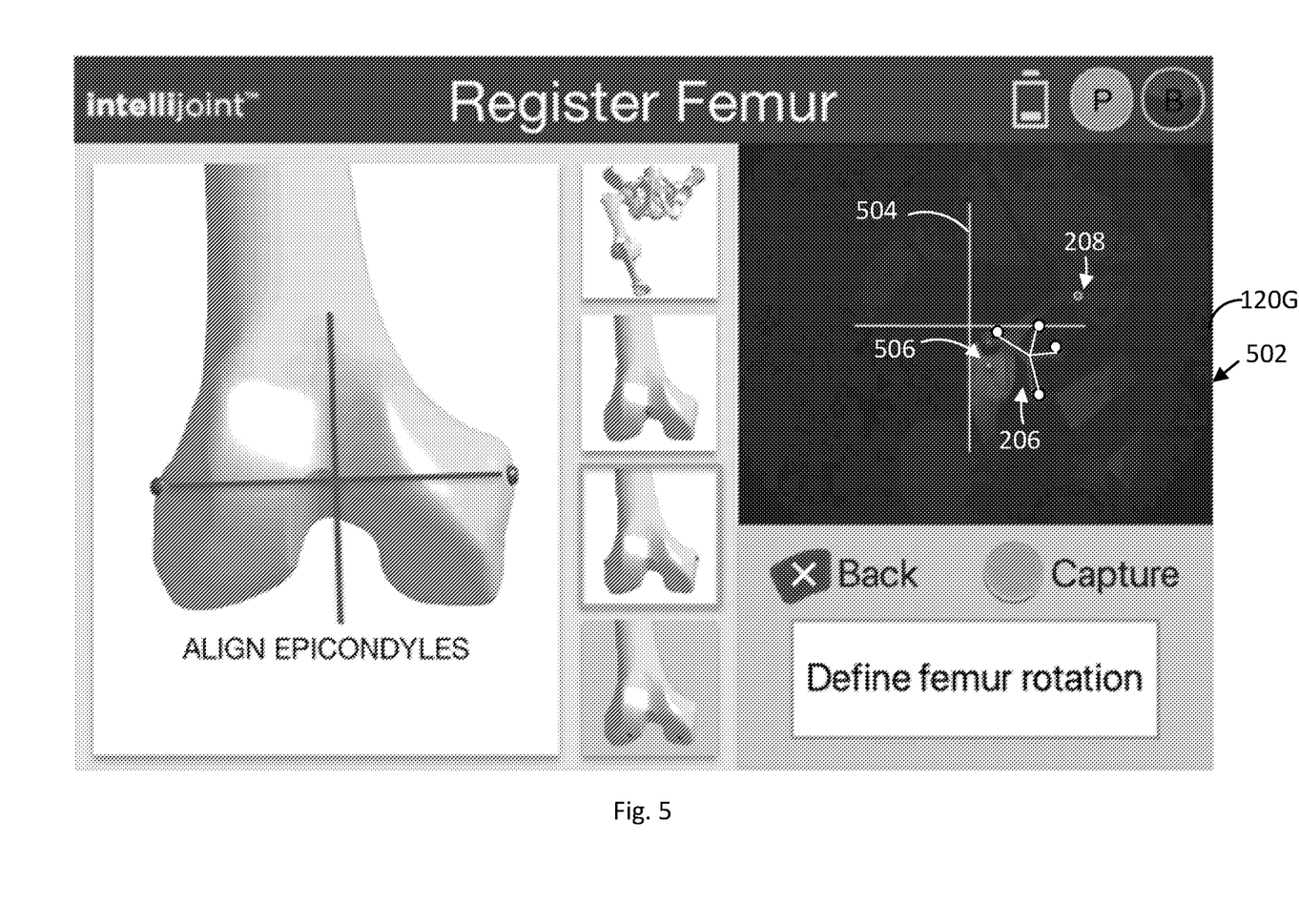
FIGS. 5, 6 and 7 are screenshots of workflow for operations to establish an rotational alignment of an anatomy a 3D space for images (e.g. register axis of the anatomy) as defined by a surgical navigation system.

The operations may display a reference point indicator for the anatomical reference point at the position, in real time, overlaid on the display of the images (in GUI 120) from the camera 104 (see FIG. 5).

It will be appreciated that the camera 104 is in a first position when input is received to define the first 3D vector and the camera 104 is in a second position, different from the first position, when input is received to define the second 3D vector thereby to provide the second 3D vector that is different from the first 3D vector.

As shown in FIG. 3 and FIG. 4, after defining the first 3D vector, operations may display a first light ray indicator 304 showing the light ray defined according to the first 3D vector, in real time, overlaid on the display of the images from the camera 104. This display of the first light ray indicator 304 may be stopped following defining the second 3D vector.

Operations provide workflow comprising instructions in a graphical user interface for a user to provide input to define the first 3D vector and the second 3D vector.

The anatomy 108 may be a femur 110 and the anatomical reference point may be a knee center. Operations may calculate an axis of the anatomy 3D vector (e.g. an axis of the femur 3D vector) using the anatomical reference point (knee center) and a second point on a distal end center such as the HCOR to define the axis of the anatomy (e.g. an axis of the femur). Operations may display an anatomy axis indicator (e.g. a femoral axis indicator) showing the axis of the anatomy defined according to the axis of the anatomy 3D vector, in real time, overlaid on the display of the images from the camera. The anatomy axis indicator is not shown in the drawings but may be similar to the first light ray indicator (i.e. a colored line rendered along the axis).

The tracker 106 may be in a position on the femur 110 proximate to the knee center to be visible in a field of view of the camera 104. In a total knee arthroplasty (TKA) or similar procedure, the camera's field of view is generally oriented to the knee. Positioning the tracker 106 proximal to the knee and distal from the hip 111 assists to keep the tracker 106 in view.

Following the definition of the first 3D vector, it may be assistive to show a candidate position for the point of interest during alignment of the marker with the point of interest such as shown in FIG. 3. Thus operations may, prior to receiving the input for defining the second 3D vector: define a candidate 3D vector for the light ray from images received after defining the first 3D vector; calculate a candidate position of the anatomical reference point using the first 3D vector and the candidate 3D vector; and display a candidate reference point indicator for the anatomical reference point at the candidate position, in real time, overlaid on the display of the images from the camera. This candidate reference point indicator may be updated in real time as the camera is moved to align the marker and the point of interest.

Figure 6:
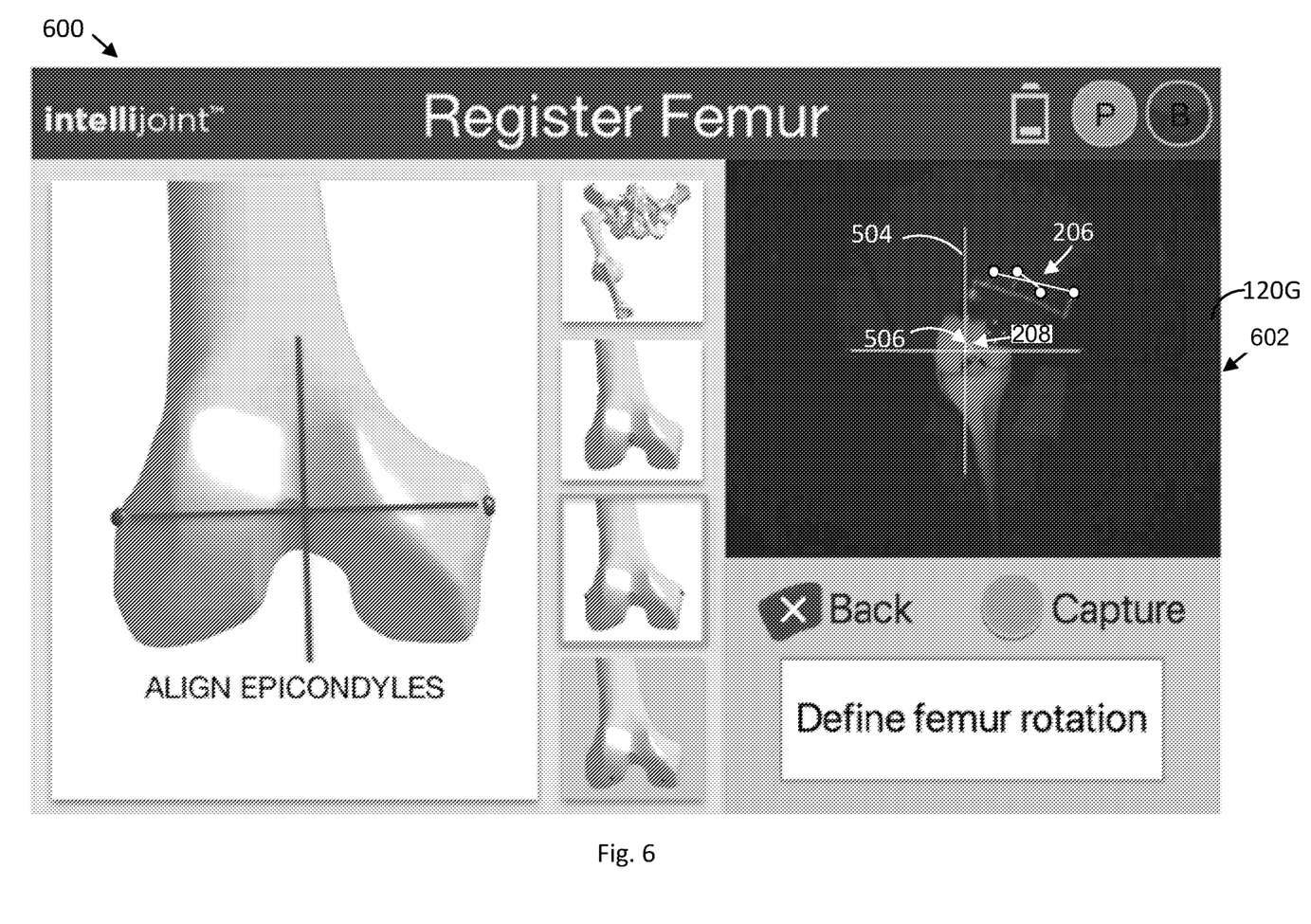
Figure 7:
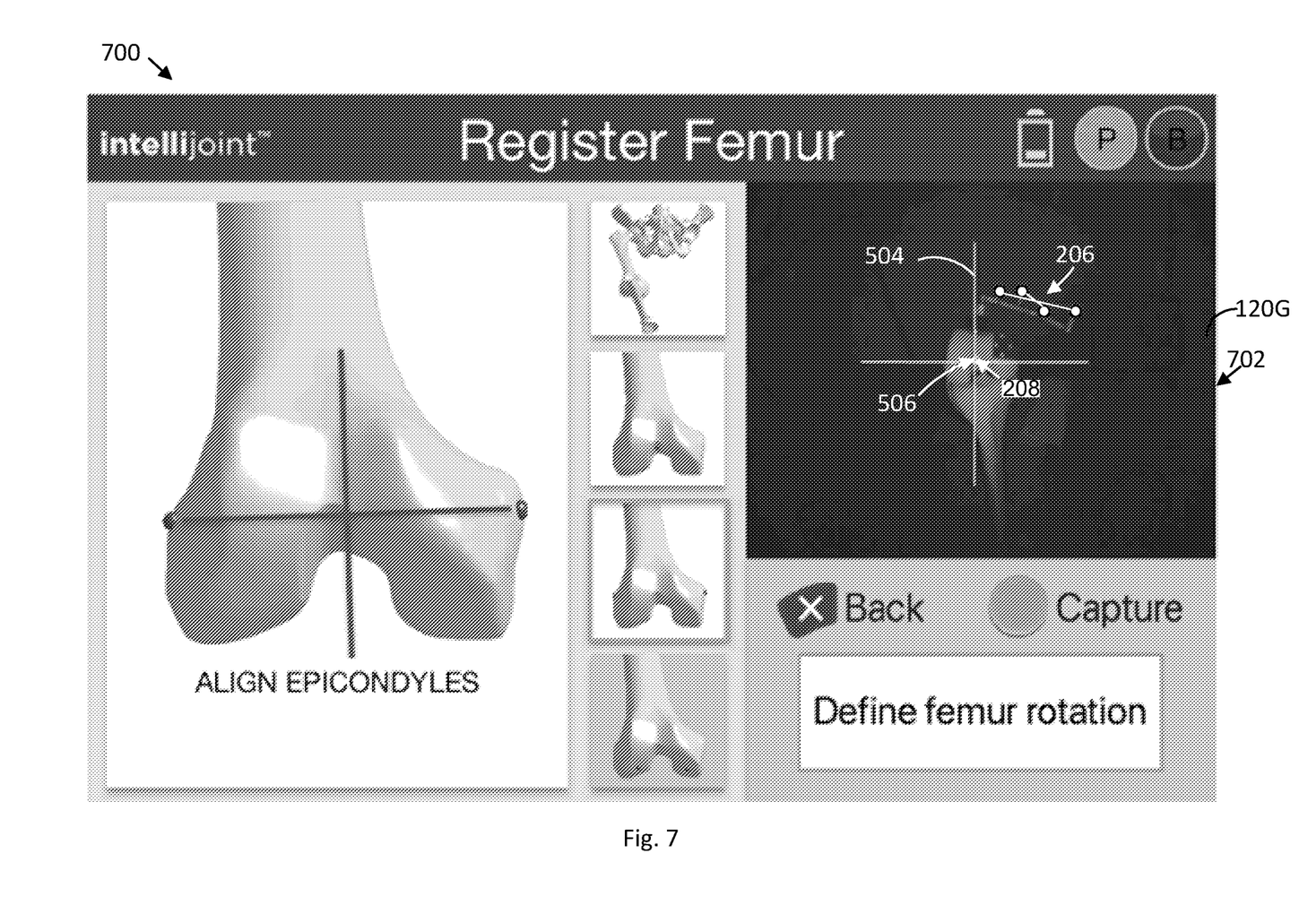

According to a second example, FIGS. 5-7 are screenshots of workflow for operations to establish a rotational alignment of an anatomy in a 3D space for images (e.g. to register one or more axes of the anatomy) as defined by a surgical navigation system. During the workflow, epicondyles of the femur 110 are aligned as shown in region 120A and sub-region 120E.

FIG. 5 shows image 502 from the camera overlaid with a Y-Z axes marker 504 (as well as graphical elements showing the knee center (a dot 506), a HCOR (an open circle 208) and the spheres of the tracker 106 (larger connected dots 206). As per screenshots of FIGS. 2-4, operations receive images of the anatomy 108 of a patient including a tracker 106 where the tracker is in a fixed position relative to the anatomy 108 and indicating its position in the image (e.g. in the 3D space).

The Y-Z axis marker 504 indicates a position of orthogonal Y-Z axes of the camera 106 where the X axis is normal thereto and coincident to the center axis of the camera 106.

With reference to FIGS. 6 and 7 showing screenshots 600 and 700 with respective images 602 and 702, the Y-Z axis is aligned with the axis of the anatomy. In the present example the anatomy is a femur 110 and the anatomical center axis is defined by a vector between the knee center and the center of hip rotation. The camera may be positioned to line up (align) the center of the Y-Z axes 504 so that the X axis is aligned with the anatomical center axis. However, to register (compute a rotational parameter for) the Y-axis for example, it is not necessary to align the X-axis at the same time or at all. The Y-Z axes are aligned with the epicondyles of the femur 110 representing the femur's Y axis. It is understood that fewer alignments (e.g. no need to align the X-axis) are necessary for registration of at least one rotational DOF.

Similar to operations to define the knee center, an input may be received when alignment is reached to capture the light ray representing the X axis. The orientation of the camera 106 is also captured to define the Y axis. Operations may also calculate a Z axis orthogonal to the other axes. The registration of the various axes to provide rotational alignment assists registration in up to define 6 DOF in any measurements (for example for surgical navigation, etc.).

The epicondyles in the images of the camera in region 120G may be indicated with graphical elements (e.g. dots) along the Y axis through the knee center (though this is not shown). The position of the epicondyles may be determined using image processing to determine the edge of the proximate end of the femur (e.g. using edge detection) and the intersection with the Y axis.

It will be appreciated that computer operations: receive images of the anatomy 110 of a patient including a tracker 106 where the tracker 106 is in a fixed position relative to the anatomy 110 to define the position of the anatomy 110 in a 3D space; display an axis marker (e.g. Y-Z axis marker 504 but it may only show one such axis e.g. a Y-axis), in real time, overlaid on a display of the images (e.g. images 502, 602, 702) in region 120G) from the camera 104, the axis marker 504 indicating a position of an axis of the camera 104 where an X axis is normal thereto and coincident to a centre axis of the camera 104; define by the processor 103, an axis in response to input received indicating the axis marker is aligned with a corresponding anatomical axis of the anatomy 108; and calculate, by the processor 103 a rotational alignment parameter using the axis in the 3D space to determine a rotational degree of freedom. The rotational alignment parameter, together with other data, may be used to measure the anatomy in up to 6 DOF. That is, the rotational alignment parameter may provide between 1 and 3 rotational DOF, with higher rotational degrees of freedom (e.g. 2 or 3 DOF) being possible if more axes are registered. It will be appreciated that when the X-axis of the camera is also aligned with the anatomical center axis, the rotational alignment parameter (or parameters) may be computed to give 3 rotational DOF (e.g. relative to the tracker in the 3D space).

Operations may display a center axis indicator for the anatomical center axis of the anatomy, in real time, overlaid on images from the camera for use to align the X-axis. In the present example the center axis indicator is the alignment of the dot representing the knee centre in the center of the circle representing the hip center of rotation. Another form of indicator may be used (e.g. when so aligned the color and or shape(s) may change).

In some examples it may be desired or sufficient to computer a rotational parameter for fewer DOF (e.g. 1 rotational) rather than 3 rotation DOF. It may be sufficient to align the Y axis without aligning the X axis.

The anatomical center axis of the anatomy (e.g. of femur 110) may be determined from two respective anatomical reference points registered to the surgical navigation system 100, the two respective anatomical reference points indicating opposite center points of the anatomy. In an example, operations may register one of the two respective anatomical reference points without using a probe as a pointer as previously described herein (e.g. in relation to the knee center or hip center of rotation).

Figure 8:
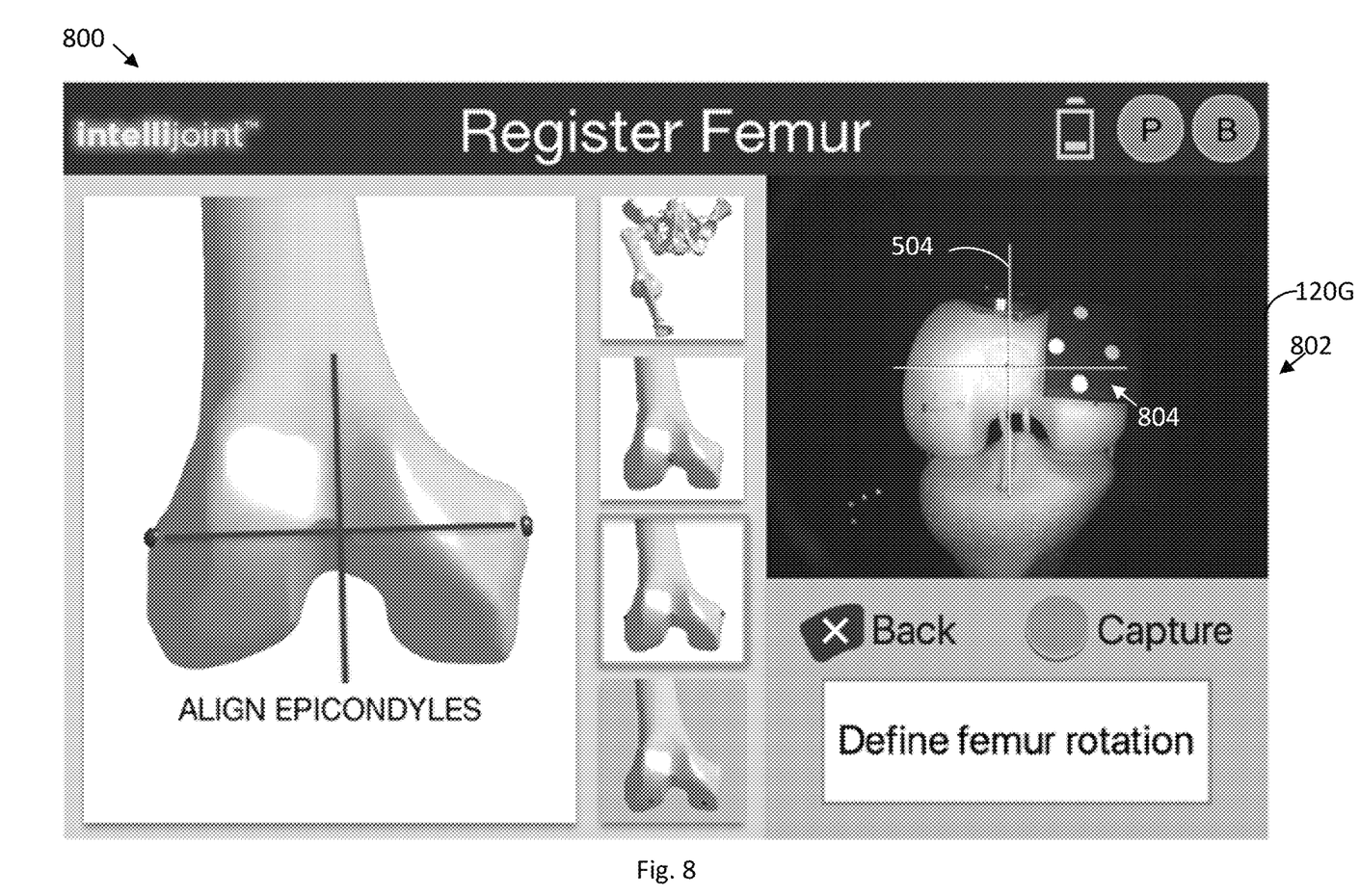
FIG. 8 is a screen shot showing a tight (up close) image of a portion of the anatomy with a second tracker much smaller in size than the tracker shown in FIG. 1 to enable tracking in up close images where the first tracker is not within the field of view.

FIG. 8 is a screenshot 800 showing a tight (up close) image 802 of a portion of the anatomy 108 with a second tracker 804 much smaller in size than the tracker 106 shown in FIG. 1 to enable tracking in up close images where the first tracker 106 is not within the field of view.

Use of a small tracker (e.g. 804) placed at or near the articular surface (e.g. proximate end of the femur 110) allows the camera 106 to be used in very close proximity to the knee. This provides the surgeon with a good view of the placements of the points on the knee, and improve accuracy of registering the points of interest (including rotational alignment) as described herein.

With reference again to FIG. 7, it will be understood that registering one or more points of interest and a rotational alignment (e.g. from Y and Z axes) may be performed in fewer operations. Following the registration of the HCOR but before registering the knee centre, the camera may be positioned to align the HCOR indicator along the anatomical axis (which would be unmarked as it is yet to be defined by the processor 103) to coincide with the knee centre. The center axis of the camera is thus along the anatomical axis. The camera is also positioned such that the targeting marker (e.g. 504) in FIG. 7 (or another such marker) is aligned along the Y axis with the epicondyles. A single input may be used to capture image registration data (store the image from the camera and invoke to processor 103 to perform its calculations and determinations) to determine the X-axis defining the anatomical axis as well as determine the Y axis to define rotational alignment. Image processing such as edge detection may be used to locate the knee centre on the proximal end of the femur and to locate the outermost end points of the epicondyles as desired. Determining the knee centre on the edge of the knee may be useful if illustrating the anatomical axis is desired or for other clinically relevant needs.

Though fewer operations are described, alignment of multiple points may be more difficult to achieve or maintain to capture the desired image. A handheld approach may still be used. It may be preferred to steady the camera. The camera may be supported by a stick (a monopod) or tripod on a hard fixed surface.

It will be apparent that a method, system, computer software (as a computer program device) may perform to: receive images from a camera 104 of an anatomy 108 of a patient including a tracker 106, 804 where the tracker 106, 804 is in a fixed position relative to the anatomy 108 and the tracker 106, 804 represents the position of the anatomy 108 in a 3D space for the images; overlay a graphical element (e.g. 204, 504) on a display of the images (e.g. in GUI 120 and region 120G), the graphical element 204, 504 representing a positional feature of the camera 104; provide workflow (e.g. software instructing the GUI, etc., as illustrated) directing an alignment of the graphical element 204, 504 with an anatomical feature of the anatomy to register the anatomy 108 in the 3D space for images defined (e.g. by the processor 103) for surgical navigation; in response to input received indicating the graphical element is aligned with the anatomical feature, capturing image registration data in accordance with position of the anatomy in the image; and registering the anatomy in the 3D space using the image registration data. The anatomical feature may be a point or may be one or more points defining an axis, etc. such that registration may register a specific point or an axis and/or rotational alignment for defining up to 6 DOF.

A number of benefits may be achieved using the techniques herein such as but not limited to: reduced system components such as the elimination of registration using a probe with tracker; easy to hold camera to align rather than probe, where the camera is located in the sterile field of a surgical procedure; only need to point camera at target with the bone reference tracker in view, rather than use a normal probe while keeping the probe and bone reference trackers in view of the camera. Operations may provide a view of the knee and collected points (e.g. as indicated by graphical elements overlaid on images as they are captured). By using the camera to probe, a better view of the knee may be obtained with a tighter shot instead of a farther shot that includes two trackers.

In addition to computing device aspects, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects stored herein.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. A method to establish an anatomical reference point in a 3D space for images as defined by a surgical navigation system having a processing device coupled to a camera, the method comprising:
    receiving, at the processing device, images of an anatomy of a patient including a tracker where the tracker is in a fixed position relative to the anatomy thereby to define a position of the anatomy in the 3D space;
    displaying, by the processing device, a targeting marker, in real time, overlaid on a display of the images from the camera, the targeting marker indicating a position of a light ray in the images;
    defining, by the processing device, a first 3D vector relative to the 3D space for the light ray in response to input received indicating the light ray is aligned with an anatomical reference point relative to the anatomy;
    after defining the first 3D vector: displaying, by the processing device, a first light ray indicator showing the light ray defined according to the first 3D vector, in real time, overlaid on the display of the images from the camera;
    defining, by the processing device, a second 3D vector of the light ray in response to input received indicating the light ray is aligned with the anatomical reference point and where the second 3D vector is different from the first 3D vector;
    stopping, by the processing device, the displaying of the first light ray indicator following defining the second 3D vector; and
    calculating, by the processing device, a position in the 3D space of the anatomical reference point using the first 3D vector and the second 3D vector.

2. The method of claim 1 comprising displaying, by the processing device, a reference point indicator for the anatomical reference point at the position, in real time, overlaid on the display of the images from the camera.

3. The method of claim 1, wherein the camera is in a first position when input is received to define the first 3D vector and the camera is in a second position when input is received to define the second 3D vector thereby to provide the second 3D vector that is different from the first 3D vector.

4. The method of claim 1 comprising providing workflow comprising instructions in a graphical user interface for a user to provide input to define the first 3D vector and the second 3D vector.

5. The method of claim 1 wherein the anatomy is a femur and the anatomical reference point is a knee center.

6. The method of claim 5, wherein the tracker is in a position on the femur, proximate to the knee center, to be visible in a field of view of the camera.

7. The method of claim 5 comprising calculating, by the processing device, an axis of the femur 3D vector using the anatomical reference point and a hip center of rotation to define the axis of the femur.

8. The method of claim 7 comprising displaying, by the processing device, a femoral axis indicator showing the axis of the femur defined according to the axis of the femur 3D vector, in real time, overlaid on the display of the images from the camera.

9. The method of claim 1 comprising, prior to receiving the input for defining the second 3D vector:
    defining, by the processing device, a candidate 3D vector for the light ray from images received after defining the first 3D vector; and
    calculating a candidate position of the anatomical reference point using the first 3D vector and the candidate 3D vector; and
    displaying, by the processing device, a candidate reference point indicator for the anatomical reference point at the candidate position, in real time, overlaid on the display of the images from the camera.

* * * * *